United States Patent [19]

Berry et al.

[11] Patent Number: 4,784,857
[45] Date of Patent: Nov. 15, 1988

[54] DRUG DELIVERY DEVICE, ITS PREPARATION AND USE

[75] Inventors: Peter W. Berry; Paul Holden, both of Herts, United Kingdom

[73] Assignee: Smith and Nephew Associated Companies PLC, United Kingdom

[21] Appl. No.: 57,904

[22] Filed: Jun. 2, 1987

[30] Foreign Application Priority Data

Jun. 3, 1986 [GB] United Kingdom ............... 8613382
Aug. 13, 1986 [GB] United Kingdom ............... 8619702
Aug. 20, 1986 [GB] United Kingdom ............... 8620226
Mar. 2, 1987 [GB] United Kingdom ............... 8706780

[51] Int. Cl.$^4$ ............................................. A61F 13/00
[52] U.S. Cl. .................................. 424/449; 424/456; 424/443; 424/445
[58] Field of Search ............... 424/443, 445, 449, 486

[56] References Cited

U.S. PATENT DOCUMENTS 3,287,222 11/1966 Larde et al. ..................... 424/445
3,875,300 4/1975 Homm et al. ................. 424/444 X
4,136,145 1/1979 Fuchs et al. .................. 424/443 X
4,136,162 1/1979 Fuchs et al. ..................... 424/443

Primary Examiner—Thurman K. Page
Assistant Examiner—L. R. House
Attorney, Agent, or Firm—Jacobs & Jacobs

[57] ABSTRACT

A device suitable for the topical administration of a pharmacologically active agent to an animal is described. The device comprises an active agent impermeable barrier layer, a reservoir containing the active agent which is in contact with the inner surface of the barrier layer and a removable protector layer in contact with the other surface of the reservoir. The reservoir comprises a fibrous mat into which the pharmacologically active agent is incorporated either by dissolving in the polymer forming the mat or by impregnation of a preformed mat. Alternative forms of the reservoir comprise a fibre mat coated on a skin contacting surface with a pressure sensitive adhesive and a fibre mat contained within a gel matrix. The device may be used to deliver nitroglycerin, oxybutynin or phenazocine transdermally.

12 Claims, 1 Drawing Sheet

DRUG DELIVERY DEVICE, ITS PREPARATION AND USE

The present invention relates to a device suitable for the topical administration of a pharmacologically active agent to an animal in which the device comprises an active agent impermeable barrier layer, a reservoir containing the active agent which contacts the inner surface of the barrier layer and a protector layer removably in contact with the other surface of the reservoir. The device allows for the controlled administration of the active agent to the animal through the skin or mucosa over a period of time.

Devices which provide a controlled continuous administration of pharmacologically active agents through the skin or mucosa are known in the art. Such devices are described in for example British Pat. Nos. 1510569, 1511121, 1577259, 2021950, 2081582, 2093694 and 2100605, European Pat. Nos. 13606, 33615 and 127282 and U.S. Pat. Nos. 3,598,122, 3,598,123, 3,734,097, 3,742,951, 3,797,494, 3,926,188, 3,942,751, 3,996,934, 4,031,894, 4,060,084 and 4,291,015. Characteristically these devices contain an active agent impermeable barrier layer which defines the outer surface of the device and a membrane sealed to the barrier layer in such a way as to create a space between them into which is placed a reservoir containing the active agent.

The membrane may also comprise an adhesive coated polymer or an adhesive layer. The active agent is typically held in a carrier which may be a liquid, semiliquid or single solid piece of polymer. The active agent is placed between the barrier layer and the release controlling layer. Alternatively, the active agent is contained within a plurality of microcapsules which are distributed throughout a permeable adhesive layer.

Although such devices are effective in use they are often difficult to manufacture especially when the reservoir is in the form of a solid film wherein difficulties may be encountered in removing casting solvents or in uniformally impregnating a pre-formed film with the active agent. I have now found that if the reservoir containing the active agent is in the form of a fibre mat, a device is provided which is simpler to manufacture in terms of removing solvent or impregnation with the active agent. It use it is found that the release of the active agent is constant and reproducible, and additionally the active agent has a less distance to diffuse before being released to the skin.

Accordingly the present invention provides a device suitable for the topical administration of a pharmacologically active agent comprising an active agent impermeable barrier layer, a reservoir comprising a fibre mat containing the pharmacologically active agent having one surface in contact with the inner surface of the barrier layer and a protector layer removably in contact with the other surface of the reservoir.

The fibre used to form the mat will contain a material which is capable of absorbing and then releasing the active agent. Suitable materials include natural and synthetic fibres. Aptly the fibre will be a synthetic fibre, since synthetic fibres are more likely to be soluble in volatile organic solvents and so would be more amenable to a process of forming the fibre mat by spraying. Suitably the fibre may be formed from a polyurethane and preferably the polyurethane will be a thermoplastic polyether or polyester polyurethane such as an Estane (trade mark) or a hydrophilic polyurethane which contains from 10 to 90% by weight of water when hydrated and preferably contains from 20 to 40% by weight of water when hydrated. Preferred hydrophilic polyurethanes are described in United Kingdom Pat. No. 2093190B.

Suitably the fibre mat may have a weight per unit area of from 5 to 500 gsm, more suitably from 100 to 300 gsm and preferably from 150 to 250 gsm for example 175 gsm, 200 gsm and 225 gsm.

The active agent may be introduced into the fibre mat either by dissolving it into the polymer solution before spraying or by impregnation by allowing the mat to stand in a solution of the agent, removing it and allowing it to dry.

The amount of active agent required to be taken up into the fibre mat will depend upon the active agent and the rate of which the active agent is to be released to the body during the time which the device is in place on the skin and also on the area of the fibre mat which is to contact the skin. In order to provide a constant rate of release approximately 10 to 20% of the active agent impregnated in the fibre mat is expected to be released to the skin.

A pharmacologically active agent means when used herein an agent which has a systemmic effect when absorbed via the skin or mucosa.

The pharmacologically active agent which is released by the devices of the present invention may be any of those which are suitable for transdermal or transmucosal delivery and include as a generic list antihypertensives, vasodilators, migraine drugs, corticosteroids, contraceptives, analgesics, antiinflammatories, anticholenergics, bronchodilators, diuretics, antihistamines, sedatives/hypnotics, tranquillizers, hormones, antidiabetics, antibiotics, antidepressants, anticonvulsants, anaesthetics, antifungals, vitamins, antielepitcs, muscle relaxants and antivirals. However, preferred active agents are nitroglycerin, clonidine, scopolamine, isosorbide dinitrate, pentaerythritol tetranitrate, estradiol, indomethacin, verapamil, propranolol, oxybutynin and phenazocine. The devices of the present invention are particularly suitable for the transdermal delivery of nitroglycerin, oxybutynin and phenazocine.

In one preferred aspect therefore the present invention provides a device suitable for the transdermal administration of nitroglycerin comprising an impermeable barrier layer, a reservoir comprising a fibre mat containing nitroglycerin having one surface in contact with the inner surface of the barrier layer and a protector layer removably in contact with the second surface of the reservoir.

In a another preferred aspect therefore the present invention provides a device suitable for the transdermal administration of oxybutynin comprising an impermeable barrier layer, a reservoir comprising a fibre mat containing oxybutynin having one surface in contact with the inner surface of the barrier layer and a protector layer removably in contact with the second surface of the reservoir.

Oxybutynin is 4-(diethylamino)-2-butynyl $\alpha$-phenylcyclohexaneglycolate and is a base capable of forming acid addition salts with organic and mineral acids, for example with hydrochloric acid to form oxybutynin chloride. Preferably the device contains oxybutynin as the free base which is observed to provide surprisingly good penetration of the skin for the active compound.

The amount of oxybutynin required to be taken up into the fibre mat will be such as to give a daily dose of up to 15 mg. For example for a device which is capable of delivering 0.1 mg/cm$^2$/day the daily dose of 10mg would require a device with an area of 10 cm × 10 cm in contact with the skin.

The transdermal delivery of oxybutynin or a pharmaceutically acceptable acid addition salt thereof has not hitherto been disclosed.

In a further preferred aspect therefore the present invention provides a device suitable for the transdermal administration of phenazocine or a pharmaceutically acceptable acid addition salt thereof comprising an impermeable barrier layer, a reservoir comprising a fibre mat containing phenazocine or salt thereof having one surface in contact with the inner surface of the barrier layer and a protector layer removably in contact with the second surface of the reservoir.

Phenazocine is 1,2,3,4,5,6-hexahydro-6, 11-dimethyl-3-(2-phenethyl)-2-,6-methano-3-benzazocin -8-ol and is a base capable of forming acid addition salts with organic and mineral acids, for example with hydrobromic acid to form phenazocine hydrobromide. Phenazocine is available in (+), (−) and racemic forms, all of which are suitable for use in the devices of the invention. Preferably the device contains phenazocine as the free base which is observed to provide surprisingly good penetration of the skin for the active compound.

The amount of phenazocine required to be taken up into the fibre mat will be such as to give a daily dose of up to 20–30 mg. For example for a device which is capable of delivering 0.1 mg/cm$^2$/day, the daily dose of 20–30 mg would require a device in which an area of 20 cm × 20 cm is in contact with the skin.

Aptly the barrier layer may comprise a backing film coated on its inner surface by an adhesive.

The backing film used in the impermeable barrier layer may be any of the conventional backing films used in the art. Useful materials for forming the backing film include metal foils such as aluminium foil, polyolefins such as polyethylene and polypropylene, polyesters such as polyethylene terephthalate, polyamide such as nylon, polyvinyl chloride, metallised polymers such as polyester film coated with aluminium.

The inner surface of the backing film of the impermeable barrier layer may be coated with an adhesive which may serve the following purposes, (a) to adhere the dressing to the skin (b) to adhere the reservoir to the impermeable barrier layer and (c) to act as an additional impermeable barrier to migration of the active agent. Preferably the adhesive is a pressure sensitive adhesive suitable for contact with the skin or mucosa. Examples of suitable adhesives include natural rubber adhesives, synthetic rubber adhesives, acrylic ester copolymer adhesives and polyvinyl alkyl ether adhesives. The weight per unit area of this adhesive layer may suitably be from 25 gsm to 75 gsm, more suitably be from 28 to 50 gsm, and preferably 30 to 45 gsm.

In one preferred embodiment of the device of the present invention the barrier layer will extend beyond the periphery of the fibre mat to provide a margin of the adhesive coated barrier layer exposed all around the fibre mat so that the device may be adhered to the skin and will be sealed around the whole of the periphery of the fibre mat.

In a second preferred embodiment of the device of the present invention the barrier layer and the fibre mat will have substantially the same dimensions. The outer surface of the barrier layer will then be in contact with a cover layer which comprises a backing layer and an adhesive layer. Suitably the cover layer will be larger than the barrier layer and will extend peripherally beyond it, all around its periphery. The cover layer may be employed to keep the barrier layer and fibre mat in position on the skin. The backing film of the cover layer may be formed from flexible, conformable materials which include woven or non-woven fabrics, microporous films or moisture vapour permeable films. The adhesive used to coat the cover layer will be a skin compatible adhesive as hereinbefore described.

In a favoured aspect of the present invention the reservoir may comprise a fibre mat carrying on its skin contacting surface an adhesive. The adhesive is present to ensure good contact between the fibre mat and the skin. The adhesive will of course be permeable to the active agent and may be used to control release of the active agent to the skin. However, it is much preferred to choose the adhesive so that no delay is imparted to the release of the migrating active agent. This may be achieved by limiting the weight per unit area of the adhesive to below 25 gsm, more suitably below 20 gsm, and preferably below 12 gsm or by selecting an adhesive of high permeability to the active agent. The adhesive is preferably applied to the mat and is present on the mat as a continuous film. Any of the well-known dermatologically acceptable pressure sensitive adhesives which permit migration of the active agent through them may be used in the devices of the present invention. Suitable adhesives include polyvinyl alkyl ether adhesives and acrylic ester copolymer adhesives. Preferred adhesives are those described in British Pat. No. 1280631 and European Pat. No. 35399. A particularly preferred is Adhesive Composition A of British Pat. No. 1280631.

The skin contacting adhesive layer may contain some of the active agent when the device is placed on the skin. This provides an initial drug presence at the surfaceof the skin and so keeps to a minimum any delay in commencement of absorption of the active agent through the skin.

If the active agent is in the form of a free base as with for example oxybutynin or phenazocine, care must be taken to avoid using an adhesive which might interact with the active agent thus acidic adhesives are to be avoided in that case.

When present the exposed adhesive surfaces of the impermeable barrier layer and/or fibre mat may be covered by a protector layer. The protector layer may be any of those which are conventionally used with adhesive dressings and which are impermeable to the active agent. A suitable protector layer is a silicone coated paper.

The devices of the present invention may be sterilised by conventional means compatible with the medicament they contain. The sterile devices may be packaged and sealed in conventional bacterial proof packs until required for use. The devices may be sterilised after sealing in the packs.

The devices of the present invention may be prepared by forming a solution of the polymer which is to form the fibre mat in a suitable solvent and at a solids content to provide the solution with an appropriate viscosity. This solution is then sprayed from a conventional spray gun positioned at a distance from a collecting surface whereby sufficient solvent evaporates from the solution in flight so and dried. A preformed layer of adhesive may be transfer coated onto one surface of the fibre mat and covered by the protector layer. The barrier may be prepared by coating onto the backing layer a film of an adhesive and the barrier layer may the be cut into pieces of the appropriate size. The non-adhesive coated side of the fibre mat is then adhered in the appropriate position on the adhesive surface of the barrier layer whereby any exposed adhesive on the barrier layer will be covered by the protective layer. The device within its package may be sterilised by a means which is compatible with the active agent. In use the device is removed from the the pack, the protector layer is removed and the device is placed on the skin.

In another aspect therefore the present invention provides a method of treatment of an animal by applying to the skin or mucosa of the animal a device containing a pharmacologically active agent which device is as hereinbefore described.

The amount and release rate of the pharmacologically active agent in the device is selected so that one device may be used in for example a 12 hour or 24 hour period and then discarded. It is a further advantage of the devices of the present invention that the fibre mats may be made easily in varying sizes.

However, the skilled worker will appreciate that under certain circumstances more than one device may be applied simultaneously.

In an alternative embodiment the reservoir may comprise a fibre mat supported in a polymer matrix which is permeable to the pharmacologically active agent at the matrix skin interface. Suitable polymer matrices include semi-solids and gels. A preferred matrix is a gel and particularly preferred is silicone gel for example Dow Corning Q7-2218 silicone gel. Devices containing the gel may be prepared by vacuum moulding the barrier layer in the form of a trough with a surround which may be adhesive coated. The trough may be rectangular, square or circular in shape. A layer of the silicone gel mix is then placed in the bottom of the trough. The gel mix is partially cured and a layer of the fibre mat carrying the pharmacologically active agent is placed onto partially cured silicone gel. A final layer of silicone gel mix is placed over the fibre mat so that its surface is level with the adhesive coated surround of the barrier layer. The silicone gel mix is then fully cured. The surface of the gel may be covered by a pharmacologically active agent impermeable protector layer. In use the gel surface is placed in contact with the skin and provides good contact between the reservoir and skin.

Preferred embodiments of device of the present invention will be described by way of example only and with respect to the following drawings.

BRIEF DESCRIPTION OF THE DRAWINGS

FIG. 1 shows a cross-section through a device (1) of the present invention in which the impermeable barrier layer (2) comprises a backing layer (3) formed from aluminium foil/polyester film laminate coated on its inner surface with a layer of adhesive (4) which is a polyvinyl ethyl ether adhesive spread as a continuous layer at a weight per unit area of 30 gsm. The reservoir (5) containing the pharmacologically active agent is adhered to the barrier layer (2) by means of the adhesive (4). The reservoir (5) is in the form of a fibre mat formed from a thermoplastic polyurethane.

Figure 1:
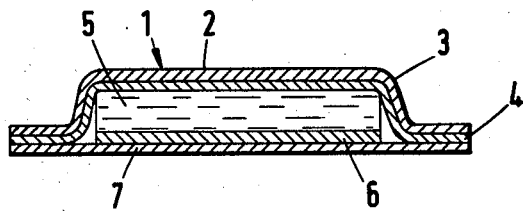
FIG. 1 shows a cross-section through a device according to the present invention in which the barrier layer extends beyond the periphery of the reservoir.

A layer of adhesive (6) is present at the other side of the reservoir (5) which permits the device (1) to be adhered in close contact with the skin. The adhesive (6) is a skin compatible pressure sensitive adhesive and can be a polyvinyl ethyl ether adhesive spread as a continuous layer at a weight per unit area of 10 gsm so as not to retard the migration of the active ingredient from the reservoir (5). The exposed adhesive surfaces of adhesive layers (4,6) are covered by a protector layer (7) which is removable in use and comprises a silicone coated release paper.

Figure 2:
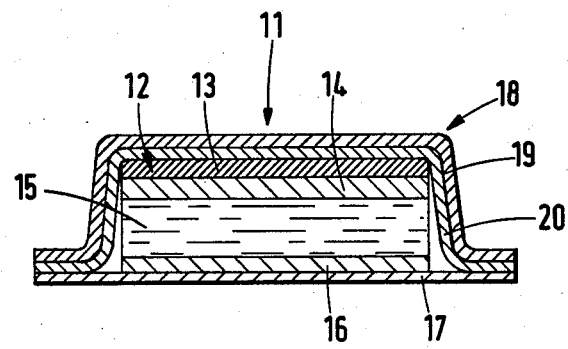
FIG. 2 shows a cross-section through a device which is adhered to the skin by means of an additional covering layer.

FIG. 2 shows a cross-section through a second preferred embodiment of the device (11) of the present invention in which there is additionally present an adhesive coated cover layer (18) comprising a backing layer (19) which may be formed from a porous film such as a non-woven fabric or a microporous film such as a plasticised polyvinyl chloride or a moisture vapour permeable film such as polyurethane. The adhesive layer (20) is formed from a skin compatible pressure sensitive adhesive as hereinbefore described. The impermeable barrier layer (12) comprises a backing layer (13) formed from an aluminium foil/polyester film laminate coated on its inner surface with a layer of adhesive (14) spread as a continuous layer.

In this embodiment the barrier layer (12) and the fibre mat (15) are substantially the same size. The reservoir (15) containing the pharmacologically active agent is in the form of an adhesive coated fibre mat formed from fibres of a thermoplastic polyurethane. A layer of adhesive (16) is present at the side of the reservoir (15) which permits the device (11) to be adhered in close contact with the skin. The exposed adhesive surfaces of adhesive layers (14,16) are covered by a protector layer (17).

Figure 3:
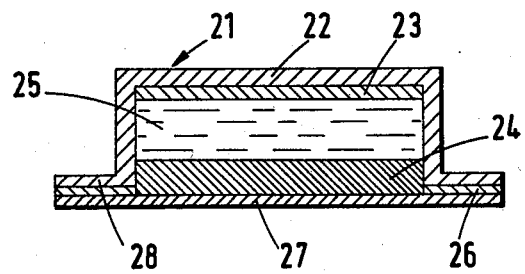
FIG. 3 shows a cross-section through a device in which the fibre mat is within a gel matrix.

FIG. 3 shows a cross-section through a third preferred embodiment of the device (21) of the present invention in which the barrier layer (22) comprises a vacuum moulded piece having a trough and a surround (28). The trough may be any shape but conventional geometric shapes such as rectangular, square or circular, are preferred. Typically the trough is circular having a depth of 1 cm and a diameter of 5 cm. The base of the trough is covered by a layer of silicone gel (23) comprising about 1 cm$^3$ in volume. The fibre mat layer (25) containing the medicament, for example nitroglycerin, is placed on top of the layer of silicone gel (23). A further layer of silicone gel (24) is placed on the fibre mat (25) and comprises a volume of about 2 cm$^3$. The face of the silica gel layer (24) should lie in a plane with the adhesive layer (26) so that good contact between the gel and the skin is achieved. The surround to the barrier layer (28) is coated on its surface with a pressure sensitive adhesive layer (26) for adhering the device to the skin. The device may be covered by a protector (27) prior to use. The adhesive layer (26) may extend over the silica gel layer (24) but this is not preferred as an extra barrier to diffusion of the medicament is introduced.

EXAMPLE 1

A solution of thermoplastic linear polyether polyurethane (130 g) is prepared by dissolving the polyurethane in tetrahydrofuran (760 g) and acetone (208 g). The solution has a solids content of 11.3% wt/wt (approx.). The solution is placed in the feed reservoir of a Bink Bullow Type 630 gravity feed, air driven spray gun which is placed approximately 12 in. from a silicone coated release paper, Steralease 05 (trade mark), which is approximately 100×25 cm in dimension. The solution is sprayed and the fibres formed by evaporation of the solvent collected on the release paper. This process provides a polyurethane fibre mat having a weight per unit area of 175 gsm. the fibre mat is allowed to dry, that is any residual solvent is allowed to evaporate, by standing in air overnight at ambient room temperature or by passing through a conventional air drying tunnel. The fibre mat is cut into pieces of size 7 cm×7 cm.

Each piece of the fibre mat is weighed and impregnated using 50 ml of a 1000 ppm aqueous solution of nitroglycerin containing 6% propylene glycol/ethanol for each 100 mg of the sample. The impregnated mats are left in the solution for 18 hours, removed, blotted dry and allowed to dry in air at ambient room temperature.

A layer of polyvinylethyl ether pressure sensitive adhesive, for example adhesive composition A of British Pat. No. 1280631, is formed by casting a solution of the adhesive in petroleum ether onto a silicone release paper. The layer so formed is transfer coated onto one surface of the nitroglycerin impregnated polyurethane fibre mat. The adhesive layer has a weight per unit area of 10 gsm.

An impermeable barrier backing layer is prepared by transfer coating a layer of polyvinyl ethyl ether pressure sensitive adhesive in petroleum ether onto the polyester surface of a metallised polyester film, Melinex (trade mark). The adhesive coating has a weight per unit area of 30 gsm. The adhesive coated film is cut into pieces 9 cm×9 cm and the non-adhesive side of the adhesive coated polyurethane fibre mat is placed centrally onto the adhesive coated film so that a 1 cm adhesive coated margin is present beyond the perimeter of the fibre mat.

A silicone release paper is now placed over the exposed adhesive surfaces of the barrier layer and fibre mat. The dressing may be placed in a View-Pack pouch (trade mark) and sealed.

In use the device is removed from the pack, the silicone release paper is removed from the adhesive surface and the device is adhered to the skin. The device will typically remain in place from 12 to 24 hours.

EXAMPLE 2

A fibre mat is prepared in a similar manner to that described in Example 1 except that the mat as made from the fibres of a hydrophilic polyurethane prepared as described in Example 2 of United Kingdom Patent No. 2093190B and which contains approximately 25% water when hydrated.

A device is prepared in a similar manner to that described in Example 1.

EXAMPLE 3

A device is prepared in a similar manner to that described in Example 1 except that the adhesive coated impermeable barrier layer and the impregnate fibre mat are of the same shape and dimension. A cover layer comprising an adhesive coated microporous, plasticized polyvinyl chloride film (Porvic, trade mark) is adhered over the outer surface of the barrier layer and extends peripherally beyond the barrier layer.

EXAMPLE 4

A number of polypropylene containers were made by vacuum forming from a suitable sheet material. The moulds were circular having a diameter of 5 cm and a depth of 1 cm. A small volume of silicone gel (Dow Corning Q7 - 2218) was prepared by mixing the two components provided in a ratio 1:1. A portion of the silicone gel mix, about 1 cm$^3$, was added to each mould and evenly distributed about the bottom of the container. The silicone gel mix was then partially cured at 60° C. for 1 hour. A sample of nitroglycerin coated polyurethane fibre mat prepared as described in Example 1, was then added to each container on top of the partially cured silicone gel.

A further quantity of silicone gel mix, about 2 cm$^3$ was then added to each mould. The mixture was then allowed to fully cure for 72 hours at room temperature.

EXAMPLE 5

A device is prepared in a similar manner to that described in Example 1 except that the fibre mat after weighing is impregnated using an aqueous solution of oxybutynin containing 25 mg/ml. The dried mat, after impregnation, may be coated with adhesive and placed in the device as described in Example 1.

EXAMPLE 6

A device is prepared in a similar manner to that described in Example 1 except that the fibre mat after weighing is impregnated using an aqueous solution of phenazocine containing 25 mg/ml. The dried mat after impregnation may be coated wth adhesive and placed in the device as described in Example 1.

Demonstration of Effectiveness

A device prepared by the method described in Example 1 was adhered to a sheet of 20 μm thick polybutadiene film which has been observed to have simliar properties of diffusion and solubility for nitroglycerin as has the skin. The film was placed in a cell so that the non-device carrying surface of th film was in contact with 70 ml of a 50:50 ethanol : water solution. This solution has a high solubility for nitroglycerin so that it represents an infinite skin for the drug so mimicing the action of the body. The concentraton of nitroglycerin in the solution and in the device was measured at given times from when the film first contacted the solution. the results showed a steady release of nitroglycerin from the device with about 5.0 mg being released over a 24 hour period.

A device prepared by the method described in Example 4 was tested using the method described in the preceeding paragraph. The gel surface was placed in contact with the polybutadiene film. The results showed that a steady release of nitroglycerin from the device was achieved and that the gel provided a constant concentration of nitroglycerin at the gel-polymer 'skin' interface.

A device prepared by the method described in Example 5 was adhered to a sheet of 20 μm thick polybutadiene film which has been observed to have similar properties of diffusion and solubility for oxybutynin as has skin. The film was placed in a cell so that the non-device carrying surface of the film was in contact with 0.05M isotonic phosphate buffer solution. This solution has a high solubility for oxybutynin so that it represents an infinite sink for the drug so mimicing the action of the body. The concentration of oxybutynin in the solution and in the device was measured at given times from when the film first contacted the solution. The results showed a steady release of oxybutynin from the device with about 12 mg being released over a 24 hour period.

A device prepared by the method described in Example 6 was adhered to a sheet of 20 μm thick polybutadiene film which has been observed to have similar properties of diffusion and solubility for phenazocine as has skin. The film was placed in a cell so that the non-device carrying surface of the film was in contact with 0.05M isotonic phosphate buffer solution. This solution has a high solubility for phenazocine so that it represents an infinite sink for the drug so mimicing the action of the body. The concentration of phenazocine in the solution and in the device was measured at given times from when the film first contacted the solution. The results showed a steady release of phenazocine from the device with about 12 mg being released over a 24 hour period.

We claim:

1. A device suitable for the topical administration of a pharmacologically active agent comprising an active agent impermeable barrier layer, a reservoir comprising a thermoplastic polyurethane fibre mat containing the pharmacologically active agent having one surface in contact with the inner surface of the barrier layer and a protector layer removably in contact with the other surface of the reservoir.

2. A device according to claim 1 in which the fibre mat is formed from fibres of a hydrophilic polyurethane which contains from 10 to 50% by weight of water when hydrated.

3. A device according to claim 1 in which the weight per unit area of the fibre mat is from 150 to 250 gsm.

4. A device according to claim 1 in which the reservoir comprises a fibre mat coated on its body contacting surface with a layer of a pressure sensitive adhesive.

5. A device according to claim 4 in which the adhesive is present at a weight per unit area of below 25 gsm.

6. A device according to claim 4 in which the adhesive is polyvinyl ethyl ether adhesive.

7. A device according to claim 1 in which the reservoir comprises a fibre mat supported in a polymer matrix which is permeable to the pharmacologically active agent.

8. A device according to claim 7 in which the polymer matrix is silicone gel.

9. A device according to claim 1 in which the impermeable device layer has an area which extends beyond the reservoir around its periphery and is adhesive coated for adhesion to the skin.

10. A device according to claim 1 in which there is additionally present an adhesive coated cover layer which covers and extends beyond the periphery of the impermeable barrier layer.

11. A device according to claim 1 in which the barrier layer comprises a backing film coated on its inner surface with an adhesive.

12. A device according to claim 1 in which the pharmacologically active agent is selected from the group consisting of nitroglycerin, cloridine, scopolamine, isosorbide dinitrate, pentaerythritol tetranitrate, estradiol, indomethacine, verapamil, propranolol, oxybutynin and phenazocine.

* * * * *